(12) United States Patent
Brown et al.

(10) Patent No.: US 7,211,407 B2
(45) Date of Patent: May 1, 2007

(54) HIGH THROUGHPUT ASSAY SYSTEMS AND METHODS FOR IDENTIFYING AGENTS THAT ALTER SURFACE EXPRESSION OF INTEGRAL MEMBRANE PROTEINS

(75) Inventors: Arthur M. Brown, Brecksville, OH (US); Eckhard Ficker, Cleveland, OH (US); Barbara A. Wible, Cleveland, OH (US)

(73) Assignee: Chan Test, Inc., Cleveland, OH (US)

( * ) Notice: Subject to any disclaimer, the term of this patent is extended or adjusted under 35 U.S.C. 154(b) by 555 days.

(21) Appl. No.: 10/635,010

(22) Filed: Aug. 6, 2003

(65) Prior Publication Data

US 2005/0014202 A1 Jan. 20, 2005

Related U.S. Application Data

(63) Continuation-in-part of application No. 10/619,184, filed on Jul. 15, 2003, now abandoned.

(51) Int. Cl.
*G01N 33/53* (2006.01)
(52) U.S. Cl. .................. 435/7.21; 435/7.23; 435/7.24; 435/29
(58) Field of Classification Search .............. 435/7.21, 435/7.23, 7.24, 29
See application file for complete search history.

(56) References Cited

U.S. PATENT DOCUMENTS

| | | | | |
|---|---|---|---|---|
| 4,202,896 | A | 5/1980 | Gootjes | 424/250 |
| 4,476,129 | A | 10/1984 | Gootjes et al. | 424/250 |
| 4,874,765 | A | 10/1989 | Lapis et al. | 514/255 |
| 4,987,084 | A * | 1/1991 | Tedder et al. | 436/63 |
| 5,122,453 | A * | 6/1992 | Martin et al. | 435/7.24 |
| 5,397,702 | A * | 3/1995 | Cahalan et al. | 435/69.1 |
| 5,969,102 | A * | 10/1999 | Bram et al. | 530/350 |
| 6,034,066 | A * | 3/2000 | Johnson et al. | 514/18 |
| 6,187,802 | B1 | 2/2001 | Cheetham et al. | 514/370 |
| 6,743,797 | B2 | 6/2004 | Brown et al. | 514/255.04 |
| 6,979,547 | B2 * | 12/2005 | Huang | 435/7.2 |
| 7,063,953 | B2 * | 6/2006 | Qin et al. | 435/7.21 |
| 7,101,677 | B1 * | 9/2006 | Milligan et al. | 435/7.2 |
| 2002/0068305 | A1 | 6/2002 | Woska, Jr. et al. | 435/7.2 |
| 2003/0022205 | A1 | 1/2003 | Curtis | 435/6 |
| 2004/0018566 | A1 | 1/2004 | Vallone et al. | 435/7.21 |
| 2005/0014202 | A1 * | 1/2005 | Brown et al. | 435/7.2 |

FOREIGN PATENT DOCUMENTS

| | | |
|---|---|---|
| EP | 0 243 903 B1 | 11/1987 |
| WO | WO 91/01732 | 2/1991 |
| WO | WO 98/18368 | 5/1998 |

OTHER PUBLICATIONS

Barclay et al (Eds.), The Leucocyte Antigen FactsBook, Second Edition, Academic Press, 1997, pp. 189-191, 316-317, 335-336, 345-346.*
C. Funck-Brentano, "Rate-dependence of class III actions in the heart," Fundam. Clin. Pharmacol., 1993, vol. 7, pp. 51-59.
Weimin Tang et al., Development and Evaluation of High Throughput Functional Assay Methods for hERG Potassium Channel, Journ. of Biomolecular Screening, vol. 6, No. 5, 2001, pp. 325-331.
Jia Xu et al., "Ion-channel assay technologies: quo vadis?" DDT, vol. 6, No. 24, Dec. 2001, pp. 1278-1287.
André Collioud et al., "Oriented and Covalent Immobilization of Target Molecules to Solid Supports: Synthesis and Application of a Light-Activatable and Thiol-Reactive Cross-Linking Reagent," Bioconjugate Chem., vol. 4, 1993, pp. 528-536.
Lutz Schmitt et al., Specific Protein Docking to Chelator Lipid Monolayers Monitored by FT-IR Spectroscopy at the Air-Water Interface, Angew. Chem. Int. Ed. Engl., vol. 35, No. 3, 1999, pp. 317-320.
Wolfgang Schuhmann et al., "Immobilization of Enzymes on Langmuir-Blodgett Films via a Membrane-Bound Receptor. Possible Applications for Amperometric Biosensors," Adv. Mater., vol. 3, No. 7/8, 1991, pp. 388-391.
Jamie L. Vandenberg et al., "HERG$^{30}$K channels: friend and foe," Trends Pharmacol. Sci., vol. 22, 2001, pp. 240-246.
Mary-Louis Roy, PH.D. et al., "*HERG*, Primary Human Ventricular Target of the Nonsedating Antihistamine Terfenadine," Circulation, vol. 94, 1996, pp. 817-823.
Keith Finlayson et al., "[$^3$H]Dofetilide binding to HERG transfected membranes: a potential high throughput preclinical screen," Eur. J. Pharm., vol. 430, 2001, pp. 147-148.

(Continued)

*Primary Examiner*—David A. Saunders
(74) *Attorney, Agent, or Firm*—Duane Morris LLP

(57) ABSTRACT

Disclosed are high throughput assay systems and methods for identifying agents that alter the level of surface expression of integral membrane proteins, such as cardiac ion channels, in mammalian cells. Also disclosed are therapeutic methods of using agents identified using such methods.

24 Claims, No Drawings

OTHER PUBLICATIONS

Georg C. Terstappen, "Functional Analysis of Native and Recombinant Ion Channels Using a High-Capacity Nonradioactive Rubidium Efflux Assay," Annal. Biochem., vol. 272, 1999, pp. 149-155.

E.M. Vaughan Williams, "Classification of anti-arrhythmic drugs," Symposium on Cardiac Arrhythmias, Elsinore, Denmark, Apr. 23-25, 1970, pp. 449-472.

B.N. Singh et al., "A third class of anti-arrhythmic action. Effects on atrial and ventricular intracellular potentials, and other pharmacological actions on cardiac muscle, of MJ 1999 and AH 3474," Br. J. Pharmacol, vol. 39, Aug. 1970, pp. 675-689.

B.N. Singh et al., "The effect of amiodarone, a new anti-anginal drug, on cardiac miscle," Br. J. Pharmacol, vol. 39, Aug. 1970, pp. 657-667.

Koonlawee Nademanee, MD, FACC, "The Amiodarone Odyssey," J. Am. Coll. Cardiol., vol. 20, 1992, pp. 1063-1065.

Michael C. Sanguinetti et al., "Two Components of Cardiac Delayed Rectifier $K^+$ Current: Differential Sensitivity to Block by Class III Antiarrhythmic Agents," J. Gen. Physiol., vol. 96, No. 1, Jul. 1990, pp. 195-215.

Mark E. Curran et al., "A Molecular Basis for Cardiac Arrhythmia: *HERG* Mutations Cause Long QT Syndrome," Cell, vol. 80, No. 5, Mar. 10, 1995, pp. 795-803.

Jeffrey R. Balser et al., "Suppression of Time-Dependent Outward Current in Guinea Pig Ventricular Myocytes," Circ. Res., vol. 69, No. 2, Aug. 1991, pp. 519-529.

Dan M. Roden, MD, "Current Status of Class II Antiarrhythmic Drug Therapy," Am. J. Cardiol., vol. 72, No. 6, Aug. 26, 1993, pp. 44B-49B.

Luc M. Hondeghem, "Development of Class III Antiarrhythmic Agents," J. Cardiovasc. Cardiol., vol. 20 Supp. 2, 1992, pp. S17-S22.

L.M. Hondeghem, MD, PhD. et al., "Class III Antiarrhythmic Agents Have a Lot of Potential but a Long Way to Go: Reduced Effectiveness and Dangers of Reverse Use Dependence," Circulation, vol. 81, No. 2, Feb. 1990, pp. 686-690.

Tsuneaki Sadanaga, MD et al., "Clinical evaluation of the use-dependent QRS prolongation and the reverse use-dependent QT prolongation of class I and class III antiarrythmic agents and their value in predicting efficacy," Amer. Heart Journal, vol. 126, No. 1, Jul. 1993, pp. 114-121.

Nancy K. Jurkiewicz et al., "Rate-Dependent Prolongation of Cardiac Action Potentials by a Methanesulfonanilide Class III Antiarrhythmic Agent: Specific Block of Rapidly Activating Delayed Rectifier $K^+$ Current by Dofetilide," Circ. Res., vol. 72, No. 1, Jan. 1993, pp. 75-83.

Bin Lu et al., "Oriented Immobilization of Fab' Fragments on Silica Surfaces," Anal. Chem, vol. 67, No. 1, Jan. 1, 1995, pp. 83-87.

Atsuko Hikikoshi Iwane et al., "Myosin Subfragment-I Is Fully Equipped with Factors Essential for Motor Function," Biophys. Biochem. Res. Commun., vol. 230, 1997, pp. 76-80.

Kingman Ng et al., "Engineering Protein-Lipid Interactions: Targeting of Histidine-Tagged Protein to Metal-Chelating Lipid Monolayers," Langmuir, vol. 11, 1995, pp. 4048-4055.

Wolfgang Frey et al., "Two-dimensional protein crystallization via metal-ion coordination by naturally occurring surface histidines," Proc. Natl. Acad. Sci. USA, vol. 93, No. 10, May 14, 1996, pp. 4937-4941.

Elizabeth W. Kubalek et al., "Two-Dimensional Crystallization of Histidine-Tagged, HIV-1 Reverse Transcriptase Promoted by a Novel Nickel-Chelating Lipid," J. Struct. Biol., vol. 113, No. 2, Sep./Oct. 1994, pp. 117-123.

George B. Sigal et al., "A Self-Assembled Monolayer for the Binding and Study of Histidine-Tagged Proteins by Surface Plasmon Resonance," Anal. Chem., vol. 68, No. 3, Feb. 1, 1996, pp. 490-497.

Michiko Furutani et al., "Novel Mechanism Associated With an Inherited Cardiac Arrhythmia: Defective Protein Trafficking by the Mutant HERG (G601S) Potassium Channel," Circulation, vol. 99, No. 17, May 4, 1999, pp. 2290-2294.

David B. Lewis et al., "Oxygenated Analogues of 1-[2-(Diphenylmethoxy)ethyl]- and 1-[2-[Bis(4-fluorophenyl)methoxy]ethyl]-4-(3-phenylpropyl)piperazines (GBR 12935 and GBR 12909) as Potential Extended-Action Cocaine-Abuse Therapeutic Agents," J. Med. Chem., vol. 42, No. 24, Dec. 1999, pp. 5029-5042.

Aloke K. Dutta et al., "Positional Importance of the Nitrogen Atom in Novel Piperidine Analogs of GBR 12909: Affinity and Selectivity for the Dopamine Transporter," Med. Chem. Res., vol. 3, No. 4, 1993, pp. 209-222.

C. Isacke, "The Adhesion Molecule Facts Book", Second Edition, Academic Press, 2000, pp. 149-151.

\* cited by examiner

HIGH THROUGHPUT ASSAY SYSTEMS AND METHODS FOR IDENTIFYING AGENTS THAT ALTER SURFACE EXPRESSION OF INTEGRAL MEMBRANE PROTEINS

This application is a continuation-in-part of application Ser. No. 10/619,184, filed Jul. 15, 2003 now abandoned.

BACKGROUND OF THE INVENTION

1. Field of the Invention

The present invention relates to high throughput assay systems and methods for identifying agents that alter the level of surface expression of integral membrane proteins, such as cardiac ion channels, in mammalian cells. The present invention also relates to therapeutic methods of using agents identified using such methods.

2. Background of the Related Art

A. Assays

Human Ether-a-go-go Related Gene (HERG) is the pore-forming potassium channel subunit that underlies the cardiac repolarizing current $I_{Kr}$, and consists of six transmembrane segments (S1–S6) and cytoplasmic amino- and carboxyl-termini. HERG has been linked to both congenital and drug-induced long QT syndrome, a serious and potential fatal heart condition.

Mutations in hERG produce functionally impaired channels and/or trafficking defective channels, both of which reduce $I_{Kr}$ currents. Mutations spanning most of the molecule have been identified in different long QT families. This suggests that hERG plays a critical role in cardiac physiology.

Most of the drugs associated with long QT syndrome (drug-induced) are hERG blockers. See, e.g., Vandenberg et al, *Trends Pharmacol Sci.* 22:240–246 (2001). Since the cardiotoxicity of the non-sedating antihistamine terfenadine (Seldane) was linked to hERG block in 1996 (see Roy et al, *Circulation* 94:817–823 (1996)), a wide variety of drugs having diverse structures, including antiarrhythmics, antibiotics, antipsychotics as well as antihistamines, have been shown to be potent hERG blockers.

Accordingly, hERG has become an important target for cardiac safety testing of new therapeutic agents. The US Food & Drug Administration currently recommends that pharmaceutical companies seeking approval for novel therapeutic compounds have them screened for potential hERG blocking.

Presently, hERG cardiac safety testing involves eletrophysiology and consists of patch clamp recording of hERG currents in HEK 293 cells which stably overexpress hERG. This assay, however, is expensive, time-consuming and requires considerable expertise. Consequently, it is usually done relatively late in the drug development process. Unfortunately, at that time, discovery that a novel therapeutic compound is a potent hERG blocker would be potentially devastating to the prospects of that compound being approved and used therapeutically. As a result, there is considerable interest in the pharmaceutical industry for assays for hERG blockers that are both less expensive and faster, and that can be employed much earlier in the drug development process.

The limitations of the patch clamp assay has led to alternative methods for preclinical screening of drugs for potential hERG interactions. Several methods have been described, but are limited, for example, in sensitivity, throughput capacity and/or false-postive rates (see Xu et al., *Drug Discover Today* 6:1278–1287 (2001)).

For example, one type of assay uses membrane potential sensitive fluorescent dyes, such as $DiBAC_4$ or FMP. Since these assays measure changes in membrane potential and not hERG activity, the risk of false positives (i.e. drugs which change membrane potential but do not block hERG) is great. A recent evaluation of such assays (fang et al., *J. Biomol. Screen.* 6:325–331 (2001)) indicates a signficant problem with false positives and, to a lesser extent, false negatives. In addition, sensitivity is reduced about 100-fold. Moreover, the rank order of hERG blocker potency differs with membane potential assays relative to patch clamp measurements, limiting the use of such fluorescent assays to identifying potential hERG channel blockers without providing useful information as to their potency. Finally, dye/drug interactions have also caused problems in this assay.

A second assay suggested as a potential high throughput preclinical screen for hERG interactions is $[^3H]$-dofelitide binding to membranes for hERG transfected cells. (See Finlayson etaz., *Eur. J. Pharm* 430:147–148 (2001)). This binding assay is nonfunctional and relies on the ability of drugs to compete with $[^3H]$-dofelitide for binding to hERG channels. In preliminary experiments, however, the rank order of hERG blockers identified by patch clamp methods was not replicated in the $[^3H]$-dofelitide binding assay. Also, the requirements for purified cell membranes as binding substrate and radio-labelled dofelitide limit the usefulness of this assay.

A third assay that has been suggested involves the measurement of rubidium (Rb) flux through cells expressing hERG (see Terstappen, *Anal Biochem.* 272:149–155 (1999)). These cells ate loaded with Rb channels and activated with high potassium levels, and Rb released into the medium is measured. The rank order of potency obtained by this method, however, does not correlate with patch clamp data (see Tang et al, *J. Biomol. Screen.,* 6:325–331 (2001)). In addition, throughput is limited and sensitivity reduced 10-fold.

Accordingly, there remains a need for assay systems for identifying blockers of integral membrane proteins, including cardiac ion channels such as hERG.

B. Cardiac Arrhythmias

Atrial flutter and/or atrial fibrillation (AF) are the most commonly sustained cardiac arrhythrnlas in clinical practice, and are likely to increase in prevalence with the aging of the population. Currently, AF affects more than 1 million Americans annually, represents over 5% of all admissions for cardiovascular diseases and causes more than 80,000 strokes each year in the United States. While AF is rarely a lethal arrhythmia, it is responsible for substantial morbidity and can lead to complications such as the development of congestive heart failure or thromboembolism. Currently available Class I and Class III anti-arrhythmic drugs reduce the rate of recurrence of AF, but are of limited use because of a variety of potentially adverse effects, including ventricular proarrhythmia. Because current therapy is inadequate and fraught with side effects, there is a clear need to develop new therapeutic approaches.

Ventricular fibrillation (VF) is the most common cause associated with acute myocardial infarction, ischemic coronary artery disease and congestive heart failure. As with AF, current therapy is inadequate and there is a need to develop new therapeutic approaches.

Although various anti-arrhythmic agents are now available on the market, those having both satisfactory efficacy and a high margin of safety have not been obtained. For example, anti-arrhythmic agents of Class I, according to the classification scheme of Vaughan-Williams ("Classification of antiarrhythmic drugs", Cardiac Arrhythmias, edited by: E. Sandoe, E. Flensted-Jensen, K. Olesen; Sweden, Astra, Sodertalje, pp 449–472 (1981)), which cause a selective inhibition of the maximum velocity of the upstroke of the action potential ($V_{max}$) are inadequate for preventing ventricular fibrillation because they shorten the wave length of the cardiac action potential, thereby favoring re-entry. In addition, they have problems regarding safety, i.e. they cause a depression of myocardial contractility and have a tendency to induce arrhythmias due to an inhibition of impulse conduction. The CAST (coronary artery suppression trial) study was terminated while in progress because the Class I antagonists had a higher mortality than placebo controls. β-adrenergenic receptor blockers and calcium channel ($I_{Ca}$) antagonists, which belong to Class II and Class IV, respectively, have a defect in that their effects are either limited to a certain type of arrhythmia or are contraindicated because of their cardiac depressant properties in certain patients with cardiovascular disease. Their safety, however, is higher than that of the anti-arrhythmic agents of Class I.

Anti-arrhythric agents of Class III are drugs that cause a selective prolongation of the action potential duration (APD) without a significant depression of the maximum upstroke velocity ($V_{max}$). They therefore lengthen the save length of the cardiac action potential increasing refractories, thereby antagonizing re-entry. Available drugs in this class are limited in number. Examples such as sotalol and ariodarone have been shown to possess interesting Class III properties (Singh B. N., Vaughan Williams E. M., "A third class of anti-arrhythmic action: effects on atrial and ventricular intracellular potentials and other pharmacological actions on cardiac muscle of MJ 1999 and AH 3747", Br. J. Pharmacol 39:675–689 (1970), and Singh B. N., Vaughan Williams E. M., "The effect of amiodarone, a new anti-anginal drug, on cardiac muscle", Br. J. Pharinacol 39:657–667 (1970)), but these are not selective Class III agents.

Sotalol also possesses Class II (β-adrenergic blocking) effects which may cause cardiac depression and is contraindicated in certain susceptible patients.

Amiodarone also is not a selective Class III antiarrhythmic agent because it possesses multiple electrophysiological actions and is severely limited by side effects. (Nademanee, K., "The Amiodarone Odyssey", J. Am. Coll. Cardiol. 20:1063–1065 (1992)) Drugs of this class are expected to be effective in preventing ventricular fibrillation. Selective Class III agents, by definition, are not considered to cause myocardial depression or an induction of arrhythmias due to inhibition of conduction of the action potential as seen with Class I antiarrhythmic agents.

Class III agents increase myocardial refractoriness via a prolongation of cardiac action potential duration (APD). Theoretically, prolongation of the cardiac action potential can be achieved by enhancing inward currents (i.e. Na+ or Ca$^2$+ currents; hereinafter $I_{Na}$ and $I_{Ca}$, respectively) or by reducing outward repolarizing potassium K+ currents. The delayed rectifier ($I_K$)K+ current is the main outward current involved in the overall repolarization process during the action potential plateau, whereas the transient outward ($I_{to}$) and inward rectifier ($I_{KI}$)K+ currents are responsible for the rapid initial and terminal phases of repolarization, respectively.

Cellular electrophysiologic studies have demonstrated that $I_K$ consists of two pharmacologically and kinetically distinct K+ current subtypes, $I_{Kr}$ (rapidly activating and deactivating) and $I_{Ks}$ (slowly activating and deactivating). (Sanguinetti and Jurkiewicz, "Two components of cardiac delayed rectifier K+ current. Differential sensitivity to block by Class III anti-arrhythmic agents", J Gen Physiol 96:195–215 (1990)). $I_{Kr}$ is also the product of the human ether-a-go-go gene (hERG). Expression of hERG cDNA in cell lines leads to production of the hERG current which is almost identical to $I_{Kr}$ (Curran et al., "A molecular basis for cardiac arrhythmia: hERG mutations cause long QT syndrome," Cell 80(5):795–803 (1995)).

Class III anti-arrhythmic agents currently in development, including d-sotalol, dofetilide (UK-68,798), almokalant (H234/09), E-4031 and methanesulfonamide-N-[1'-6-cyano-1,2,3,4-tetrahydro-2-naphthalenyl)-3,4-dihydro-4-hydroxyspiro[2H-1-benzopyran-2,4'-piperidin]-6yl], (+)-, monochloride (MK-499) predominantly, if not exclusively, block $I_{Kr}$. Although, amiodarone is a blocker of $I_{Ks}$ (Balser J. R. Bennett, P. B., Hondeghem, L. M. and Roden, D. M. "Suppression of time-dependent outward current in guinea pig ventricular myocytes: Actions of quinidine and amiodarone", Circ. Res. 69:519–529 (1991)), it also blocks $I_{Na}$ and $I_{Ca}$, effects thyroid function, is as a nonspecific adrenergic blocker, acts as an inhibitor of the enzyme phospholipase, and causes pulmonary fibrosis (Nademanee, K. "The Amiodarone Odessey". J. Am. Coll. Cardiol. 20:1063–1065 (1992)).

Reentrant excitation (reentry) has been shown to be a prominent mechanism underlying supraventricular arrhythmias in man. Reentrant excitation requires a critical balance between slow conduction velocity and sufficiently brief refractory periods to allow for the initiation and maintenance of multiple reentry circuits to coexist simultaneously and sustain AF. Increasing myocardial refractoriness by prolonging APD, prevents and/or terminates reentrant arrhythmias. Most selective, Class III antiarthythmic agents currently in development, such as d-sotalol and dofetilide predominantly, if not exclusively, block $I_{Kr}$, the rapidly activating component of $I_K$ found both in atrium and ventricle in man.

Since these $I_{Kr}$ blockers increase APD and refractoriness both in atria and ventricle without affecting conduction per se, theoretically they represent potential useful agents for the treatment of arrhythmias like AF and VF. These agents have a liability in that they have an enhanced risk of proarrhythmia at slow heart rates. For example, torsade de pointes, a specific type of polymorphic ventricular tachycardia which is commonly associated with excessive prolongation of the electrocardigraphic QT interval, hence termed "acquired long QT syndrome", has been observed when these compounds are utilized (Roden, D. M. "Current Status of Class III Antiarrhythrnic Drug Therapy", Am J. Cardiol, 72:44B–49B (1993)). The exaggerated effect at slow heart rates has been termed "reverse frequency-dependence" and is in contrast to frequency-independent or frequency-dependent actions. (Hondeghem, L. M., "Development of Class III Antiarrhythmic Agents", J. Cardiovasc. Cardiol. 20 (Suppl. 2):S17–S22). The pro-arrhythmic tendency led to suspension of the SWORD trial when d-sotalol had a higher mortality than placebo controls.

The slowly activating component of the delayed rectifier ($I_{Ks}$) potentially overcomes some of the limitations of $I_{Kr}$ blockers associated with ventricular arrhythmias. Because of its slow activation kinetics, however, the role of $I_{Ks}$ in atrial repolarization may be limited due to the relatively short APD of the atrium. Consequently, although $I_{Ks}$ blockers may provide distinct advantage in the case of ventricular arrhythmias, their ability to affect supra-ventricular tachyarrhythmias (SVT) is considered to be minimal.

Another major defect or limitation of most currently available Class III anti-arrythmic agents is that their effect increases or becomes more manifest at or during bradycardia or slow heart rates, and this contributes to their potential for proarrhythmia. On the other hand, during tachycardia or the conditions for which these agents or drugs are intended and most needed, they lose most of their effect. This loss or diminishment of effect at fast heart rates has been termed "reverse use-dependence" (Hondeghem and Snyders, "Class III antiarrhythmic agents have a lot of potential but a long way to go: Reduced effectiveness and dangers of reverse use dependence", *Circulation,* 81:686–690 (1990); Sadanaga et al., "Clinical evaluation of the use-dependent QRS prolongation and the reverse use-dependent QT prolongation of class III anti-arrhythmic agents and their value in predicting efficacy" *Amer. Heart Journal* 126:114–121 (1993)), or "reverse rate-dependence" (Bretano, "Rate dependence of class III actions in the heart", *Fundam. Clin. Pharmacol.* 7:51–59 (1993); Jurkiewicz and Sanguinetti, "Rate-dependent prolongation of cardiac action potentials by a methanesulfonanilide class III anti-arrhythmic agent: Specific block of rapidly activating delayed rectifier K+ current by dofetilide", *Circ. Res.* 72:75–83 (1993)). Thus, an agent that has a use-dependent or rate-dependent profile, opposite that possessed by most current class III anti-arrhythmic agents, should provide not only improved safety but also enhanced efficacy.

In view of the problems associated with current class III anti-arrhythmic agents, there remains a need for an effective treatment of cardiac arrhythrmias in mammals.

SUMMARY OF THE INVENTION

Accordingly, it is an object of the present invention to provide assays and methods for identifying agents which alter the level of surface expression of integral membrane proteins, such as cardiac ion channels. It is also an object of the present invention to provides methods of preventing or treating cardiac arthythmia.

In accordance with these and other objects, a first embodiment of the present invention is directed to a method for identifying an agent that alters the level of surface expression of an integral membrane protein in a mammalian cell, comprising: a) preparing a first medium containing mammalian cells that express a first mutant form of a membrane protein of interest, wherein this first mutant form is expressed on the surface of said cells at a level less than a wild-type form; b) adding an effective amount of a candidate agent; c) incubating the cells in the presence of the active agent for a sufficient period of time; d) adding an effective amount of at least one antibody which binds to at least one extracellular epitope of the mutant form; and e) determining the level of binding, wherein a change in said level of binding indicates that the candidate agent alters the level of surface expression.

A second embodiment of the present invention is directed to a method for preventing or treating cardiac arrhythmia comprising administering to a mammal in need thereof an effective amount of an active agent which increases the level of surface expression of a first mutant form of hERG in a mammalian cell and does not increase the level of surface of a second mutant form of hERG in a mammalian cell as determined by the method comprising: a) preparing a first medium containing mammalian cells that express a first mutant form of hERG which is expressed on the surface of the cells at a level lower than that of a wild-type form of hERG; b) adding an effective amount of the active agent; c) incubating the cells in the presence of the active agent for a sufficient period of time; d) adding an effective amount of at least one antibody which binds to at least one extracellular epitope of this mutant form of hERG; e) determining the level of binding of the antibody; f) preparing a second medium containing mammalian cells that express a second mutant form of hERG which is different from the first mutant form and is expressed on the surface of the mammalian cells at a level lower than that of a wild-type form of hERG; g) adding an effective amount of the active agent to the second medium; h) incubating the cells in the presence of the active agent for a sufficient period of time; i) adding an effective amount of at least one antibody which binds to at least one extracellular epitope of this second mutant form; and j) determining the level of binding of the antibody.

Additional advantages, objects and feature of the invention will be set forth in part in the description which follows and in part will become apparent to those having ordinary skill in the art upon examination of the following or may be learned from practice of the invention. The objects and advantages of the invention may be realized and attained as particularly pointed out in the appended claims.

DETAILED DESCRIPTION OF PREFERRED EMBODIMENTS

I. Assays and Methods of Use

Preferred embodiments of the present invention include an assay system and method for identifying an agent that binds to an integral membrane protein, such as a membrane ion channel, and thereby increase or decrease its surface expression in mammalian cells. In certain particularly preferred embodiments, the assay and system determine the ability of an agent to bind to a particular site on a mutant form of an integral membrane protein and thereby alter the surface expression thereof. Such an alteration in surface expression may result from the agent blocking a site on the mutant that corresponds to an active site on the wild-type membrane protein and/or by blocking intracellular trafficking and/or processing of the mutant membrane protein. Alternatively, an alteration in surface expression may result from the agent improving intracellular trafficking of the mutant membrane protein.

There are a wide variety of formats known and available to those skilled in the art for appropriate binding assays. According to certain embodiments of the present invention, one or more cells expressing a membrane protein of interest may be provided in a suitable liquid medium and exposed to one or more candidate compounds, while in other embodiments the cells may be immobilized on a surface. Similarly, according to still other embodiments of the invention, one or more candidate compounds may be immobilized on a surface and exposed to a liquid medium containing one or more cells that express a membrane protein of interest or the candidate compound(s) may be included in a suitable liquid medium to which one or more cells expressing a membrane protein of interest is added.

Binding is often easier to detect in systems in which at least one of the candidate compound and the membrane protein of interest is labeled (e.g., with fluorescence, radioactivity, an enzyme, an antibody, etc., including combinations thereof, as known to those skilled in the art). After exposing the candidate compound to the cell expressing a membrane protein and washing off or otherwise removing unbound reagents, the presence of the labeled moiety (i.e., bound to the unlabelled component of the test system) is measured.

Methods for performing various binding assays are known in the art, including but not limited to the assay systems such as those described in PCT Application US98/18368. Various references provide general descriptions of various formats for protein binding assays, including competitive binding assays and direct binding assays, (see e.g., Stites and Terr, *Basic and Clinical Immunology*, 7th ed. (1991); Maggio, *Enzyme Immunoassay*, CRC Press, Boca Raton, Fla. (1980); and Tijssen, *Practice and TheoLy of Enzyme Immunoassqys*, in *Laborator Teelmiques in Biochemistry and Molecular Biology*, Elsevier Science Publishers, B. V. Amsterdam, (1985)).

Particularly preferred embodiments of the present invention involve assay systems and methods to identify compounds that increase or decrease the surface expression of a membrane protein of interest by blocking the activity of the membrane protein and/or by blocking intracellular trafficking and/or processing thereof.

Thus, according to certain particularly preferred embodiments, immunoassays are provided in which one or more cells expressing a membrane protein of interest are generally bound to a suitable solid support (e.g. the well of a microtiter plate, a microcard, or any other similar format known to those skilled in the art) and combined with a candidate agent, and observing changes in the level of surface expression of the membrane protein of interest. Thus, in these preferred embodiments, one or more of the assay components are attached to a solid surface.

In some embodiments, an assay system may used (as known in the art) to detect the change in the surface expression of the membrane protein due to the binding of the candidate agent. For example, if the membrane protein of interest is a membrane ion channel, a patch clamp assay may be employed to detect a change in the flux of ions across the membrane, thus evidencing an increase in the level of surface expression of the ion channel.

In alternative embodiments, an indirect immunoassay system is used in which the membrane protein on the surface of the cell(s) is detected by the addition of one or more antibodies directed against an extracellular epitope of the membrane protein, as known in the art.

When using a solid support in the methods of the present invention, virtually any solid surface is suitable, as long as the surface material is compatible with the assay reagents and it is possible to attach the component to the surface without unduly altering the reactivity of the assay components. Those of skill in the art recognize that some components exhibit reduced activity in solid phase assays, but this is generally acceptable, as long as the activity is sufficient to be detected and/or quantified.

Suitable solid supports include, but are not limited to, any solid surface such as glass beads, planar glasses, controlled pore glasses, plastic porous plastic metals, or resins to which a material or cell may be adhered, etc.). Those of skill in the art recognize that in some embodiments, the solid supports used in the methods of the present invention may be derivatized with functional groups (e.g hydroxyls, amines, carboxyls, esters, and sulfhydryls) to provide reactive sites for the attachment of linkers or the direct attachment of the candidate agent or other assay component.

Adhesion of an assay component to a solid support can be direct (i.e. the component directly contacts the solid surface) or indirect (i.e. an agent and/or component (e.g. an antibody) is/are bound to a support, and the other assay component(s) binds to this agent or component rather than to the solid support). In some embodiments, the agent or component is covalently immobilized (e.g., utilizing single reactive thiol groups of cysteine for anchoring proteinaceous components (see e.g., *Bioconjug. Chem.*, 4:528–536 (1993)), or non-covalently, but specifically (e.g., via immobilized antibodies or other specific binding proteins (see e.g., *Adv. Mater.*, 3:388–391 (1991); *Anal. Chem.*, 67:83–87 (1995))), the biotin/streptavidin system (see e.g., *Biophys. Biochem. Res. Commun.*, 230:76–80 (1997)), or metal-chelating Langmuir-Blodgett films (see e.g., *Langmuir* 11:4048–4055 (1995); *Angew. Chem. Int. Ed. Engl.*, 35:317–320 (1996); *Proc. Natl. Acad. Si. USA* 93:4937–4941 (1996); and *J. Struct. Biol.*, 113:117–123 (1994)), and metal-chelating self-assembled monolayers (see e.g., *Anal. Chem.*, 68:490–497 (1996)), for binding of polyhistidine fusion proteins.

In some particularly preferred embodiments, standard direct or indirect ELISA, IFA, or RIA methods as generally known in the art are used to detect the binding of a candidate agent to a membrane protein of interest. In some embodiments, an increase in the level of surface expression of the membrane protein is detected in a sample, while in other embodiments, a decrease in the level of surface expression is detected. Thus, it is clear that the methods of the present invention are adaptable to the detection, identification, and characterization of multiple elements.

Accordingly, in some particularly preferred embodiments of the methods of the present invention, a sandwich ELISA (enzyme-linked immunosorbent assay) with a monoclonal or polyclonal antibody for capture ("a capture antibody") and a secondary antibody ("a reporter antibody") for detection of bound antibody-antigen complex (e.g., hERG bound to anti-hERG antibody or a hERG mutant bound to the corresponding antibody) may be used.

In some preferred ELISA embodiments, alkaline phosphatase conjugates are used, while in still other preferred embodiments, horseradish peroxidase conjugates are used. In addition, avidin/biotin systems may also be used, particularly for assay systems in which increased signal is desired. Suitable enzymes for use in preferred embodiments include, but are not limited to, peroxidases, luciferases, alkaline phosphatases, glucose oxidases, beta-galactosidases and mixtures of two or more thereof.

Thus, in one illustrative method of the present invention, 100 µl biotinylated antibody (e.g., directed against hERG or a mutant thereof) appropriately diluted in blocking buffer is added to each well of avidin-precoated ELISA plates (e.g., the neutravidin plates commercially available from Pierce). After 2 hr, the plate is washed with wash buffer (e.g., TBS/Tween 20 0.1%, with or without a blocking agent). Further nonspecific binding may be inhibited by adding blocking buffer (e.g., by adding 300 µl SuperBlock (Pierce) twice, as per the manufacturer's recommendations). Following incubation to allow binding of the biotinylated antibody to the surfaces of the wells, the plate is washed (e.g., 3 times) according to methods known in the art, to remove any unbound antibody present in the wells.

Samples of cells expressing a membrane protein of interest may be diluted with an appropriate buffer and added to the wells of the ELISA plate, as well as. standards and controls. The diluted standards, controls, and samples, may be added to the wells of the ELISA plate (e.g., 100 µl/well). Standards, controls, and samples are generally tested in duplicate. The plate is incubated, for example, overnight, or for another appropriate length of time, typically on a rocking table at 5 RPM or other suitable agitation means in a humidor or the like. The plate is washed (e.g., 3 times or the like) with washing buffer as known in the art. Then, 100 µl of appropriately diluted monoclonal or polyclonal reporter antibody (preferably preabsorbed with the antibody used to coat the wells of the plate), may be added and allowed to incubate at room temperature, preferably overnight (e.g., about 18–20 hours), or for another such incubation period as may be appropriate.

The plate may then be washed again, preferably as described above, and 100 μl enzyme-labeled antibody, such as alkaline phosphatase-conjugated anti-rabbit Ig (commercially available from Pierce), appropriately diluted in a suitable blocking buffer (e.g., BSA Blocker in TBS) may be added, and allowed to incubate for a sufficient period (e.g. 2 hours) with rocking or similar agitation as described above.

The plate may then preferably be washed again as described above. The enzyme substrate may be added to the wells and the reaction allowed to occur for an appropriate length of time, at the end of which the reaction is stopped using any appropriate method known in the art, and the optical densities of the solutions within the wells determined as known in the art.

Because background signal is often the limiting factor in amplified assays, in some embodiments of the present invention, measures may be undertaken to reduce background signal in these assays.

In addition to the assay systems in which a solid support is utilized, the present invention provides methods in which the assay components remain suspended in solution.

According to a first particularly preferred embodiment of the present invention, a method is provided for identifying an agent, such as a peptide, protein, antibody or chemical agent, that alters the level of surface expression of an integral membrane protein, such as hERG, in a mammalian cell. This method comprises: a) preparing a first medium containing mammalian cells that express a first mutant form of the membrane protein of interest, wherein this first mutant form is expressed on the surface of the cells at a level less than a wild-type form of the protein; b) adding an effective amount of a candidate agent; c) incubating the cells in the presence of the candidate agent for a sufficient period of time; d) adding an effective amount of at least one antibody which binds to at least one extracellular epitope of the mutant; and e) determining the level of binding of the antibody to the extracellular epitope of the protein following incubation of the cells with the candidate agent.

Any change, such as an increase or decrease, in the level of binding in the presence of the candidate agent relative to control indicates that the candidate agent alters the level of surface expression of the first mutant form of the membrane protein.

According to a second particularly preferred embodiment of the present invention, the above method further comprises: f) preparing a second medium containing mammalian cells that express a second mutant form of the membrane protein of interest, wherein this second mutant form is different from the first mutant form and is also expressed on the surface of said mammalian cells at a level lower than that of a wild-type form of the membrane protein; g) adding an effective amount of the candidate agent; h) incubating said cells in the presence of said candidate agent for a sufficient period of time; i) adding an effective amount of at least one antibody which binds to at least one extracellular epitope of the second mutant form; and j) determining the level of binding of the antibody to the extracellular epitope. Any change in the level of binding following incubation with the candidate agent indicates that the candidate agent alters the level of surface expression of the second mutant form of the membrane protein of interest.

According to preferred embodiments of the present invention, step (d) above comprises adding an effective amount of at least one primary antibody and an effective amount of at least one secondary antibody. According to such embodiments, the primary antibody preferably binds to at least one extracellular epitope of the first mutant form of the membrane protein of interest. Even more preferably, according to such embodiments, the secondary antibody binds to the first antibody.

According to still other preferred embodiments of the present invention, step (i) above also comprises adding an effective amount of at least one primary antibody and an effective amount of at least one secondary antibody. According to such embodiments, the primary antibody preferably binds to at least one extracellular epitope of the second mutant form of the membrane protein of interest. Even more preferably, according to such embodiments, the secondary antibody binds to the first antibody.

Preferably, the secondary antibody is coupled to an enzyme to facilitate detection and determination of the level of binding. Suitable enzymes for use in the methods of the present invention are known and available to those skilled in the art. Illustrative examples of suitable enzymes include, but are not limited to, peroxidases, luciferases, alkaline phosphatases, glucose oxidases, beta-galactosidases and mixtures of two or more thereof.

The determination of the level of surface expression of the integral membrane protein of interest may be performed using any of the methods and techniques known and available to those skilled in the art. Preferably, the level of binding is determined by fluorescence, luminescence, radioactivity, absorbance or a combination of two or more of these.

According to certain particularly preferred embodiments of the present invention, the integral membrane protein is a membrane ion channel. Illustrative examples of suitable membrane ion channels include, but are not limited to, sodium channels, potassium channels, calcium channels or chloride channels.

According to preferred embodiments of the present invention, the extracellular epitope to which the antibody binds on the first mutant form of the membrane protein is preferably the same as a wild-type epitope, i.e. an extracellular epitope found on the naturally-occurring form(s) of the membrane protein of interest. Without wishing to be bound to any theory of operability or the like, such an arrangement may have the potential to reduce errors arising from differences in protein structure, for example by a change in one or more of the functional properties of the protein.

According to still other preferred embodiments of the present invention, the extracellular epitope to which the antibody binds on the second mutant form of the membrane protein is preferably the same as a wild-type epitope.

According to particularly preferred embodiments of the present invention, the extracellular epitope on the first and/or the second mutant forms of the membrane protein contains a tag. Suitable tags are known and available to those skilled in the art. A particularly preferred tag for use in the methods of the present invention is a hemagglutinin (HA) tag. The tag may be inserted in an extracellular domain of the first and/or the second mutant forms of the membrane protein or may replace a portion of an extracellular domain thereof.

According to the methods of the present invention, the first and second mutant forms of the membrane protein preferably both differ in at least one amino acid residue from the amino acid sequence(s) of the wild-type form(s) of the membrane protein. Moreover, the first and second mutant forms also preferably differ in at least one amino acid residue from the amino acid sequence of each other.

According to certain preferred embodiments, the first mutant form of the membrane protein may be a trafficking-deficient mutant and so is expressed on the surface of mammalian cells at a level lower than a corresponding wild-type form. According to still other preferred embodiments, the second mutant form may be a trafficking-deficient mutant and according to yet still other preferred embodiments, both the first and the second mutant forms may be a trafficking-deficient mutants.

According to certain particularly preferred embodiments of the present invention, the membrane protein of interest is a cardiac ion channel, most preferably a potassium ion channel. Such ion channels are known to those skilled in the art. An illustrative example of such a potassium ion channel is hERG.

Suitable first mutant forms of hERG for use in the methods of the present invention are known to those skilled in the art. According to preferred embodiments of the present invention, such mutant forms should function when expressed on the cell surface, but should be expressed on the surface at a lower level than any wild-type form(s), most preferably due to a trafficking deficiency. Illustrative examples of suitable mutant forms include, but are not limited to, G601S (which has been identified in a long QT syndrome family) and N470D. G601S is a trafficking-deficient, hypomorphic channel which generates minimal, although kinetically unaltered, currents (see Furatani et al., *Circulation* 99:2290–2294 (1999)) and N470D is a hypomorphic missense mutation. Agents which increase surface expression of mutants such as G601S and N470D also bind to a high affinity site in the hERG ion conduction pathway and are therefore potent hERG blockers.

For purposes of illustration and not limitation, in a preferred embodiment of the present invention, a mutant form of an ion channel, such as hERG-G601S, is engineered to express an extracellular tag, such as an HA tag, in the linker between transmembrane domains S1 and S2 (such a tag preferably should not alter the functional properties of the channel). Cells, such as HEK 293 cells, stably expressing this tagged mutant, e.g. hERG-G601S-HA, are plated in a suitable container, such as a 96-well microtiter plate, and incubated with one or more candidate agents for a sufficient time, such as overnight. The cells are then preferably fixed, such as with formaldehyde, but preferably not permeabilized and antibodies recognizing the HA tag are added. A secondary antibody, preferably conjugated to an enzyme, such as horseradish peroxidase, is used to bind the anti-HA antibody(ies) bound to the surfaces of the fixed cells. Cell surface signals may then be developed by any suitable method, such as a chemiluminescent reaction mix, and the level measured, for example, in a microtiter plate luminometer. Control cells are usually incubated with water and/or any liquid vehicle used in conjunction with the candidate agent, such as DMSO. Agents which increase the surface expression of the first mutant form are potential blockers of hERG (or similar such ion channel).

Suitable second mutant forms of hERG for use in the methods of the present invention are also known to those skilled in the art. According to preferred embodiments of the present invention, such mutant forms should also be expressed on the surface at a lower level than any wild-type form(s), most preferably due to a trafficking deficiency, but should not function when expressed on the cell surface. Illustrative examples of suitable mutant forms of hERG include, but are not limited to, G601S/F656C and N470D/F656C. Agents which do not increase surface expression of mutants such as G601S/F656C and N470D/F656C are potent hERG blockers.

Again for purposes of illustration and not limitation, in a preferred embodiment of the present invention, a second mutant form of the ion channel, such as hERG-G601S/F656C, is engineered to express an extracellular tag, such as an RA tag, in the linker between transmembrane domains S1 and S2 (again, such a tag preferably should not alter the functional properties of the channel). Cells, such as HEK 293 cells, stably expressing this tagged mutant, e.g. hERG-G601S/F656C-HA, are plated in a suitable container, such as a 96-well microtiter plate, and incubated for a sufficient time with a candidate agent, preferably a candidate agents which increased surface expression of the first mutant form. The cells are then preferably fixed and not permeabilized, and primary antibodies recognizing the HA tag are added. Secondary antibodies, preferably conjugated to an enzyme are then used to bind the anti-HA antibody(ies) bound to the surfaces of the fixed cells. Cell surface signals may then be developed by any suitable method, such as a chemiluminescent reaction mix, and the level measured, for example, in a microtiter plate luminometer. Control cells are usually incubated with water and/or any liquid vehicle used in conjunction with the candidate agent, such as DMSO. Those agents which do not increase the level of surface expression of the second mutant form are likely to be potent hERG blockers. Agents which increase the level of surface expression of the first mutant form and do not increase the level of surface expression of the second mutant form are highly likely to be potent hERG blockers.

According to more particularly preferred embodiments of the above methods, hERG surface expression is assayed by removing the microtiter plate(s) from the incubator(s) and removing the media bathing the cells. The wells are rinsed three times with PBS (100 μl) and then the cell fixed with paraformaldehyde (e.g. 4% in PBS, pH 7.2, 100 μl), and then rinsed with PBS. Non-specific binding sites on the cell surface are preferably blocked, for example by incubating the cells with 1% goat serum in PBS ("blocking buffer"). After removing the blocking buffer, the cells are incubated with the primary antibody, such as rat anti-HA in blocking buffer. The primary antibody is then removed, the cells washed (e.g. 3 times with blocking buffer). Secondary antibody, such as horseradish peroxidase-conjugated anti-rat goat antibody in blocking buffer, is added. The secondary antibody is then removed and the cells preferably washed.

According to such embodiments, chemiluminescent signals may be developed using any suitable technique, such as SuperSignal ELISA Femto Maximum Sensitivity Substrate (Pierce Chemical Co.). A suitable amount of reagent, e.g. 50 μl for each well of a microtiter plate, is added and a GloRunner luminometer (Turner Designs) used to obtain the data.

A fluorescent reaction may optionally be added to monitor the number of cells per well.

II. Therapeutic Compositions and Methods

The preferred embodiments of the present invention also methods of preventing or treating cardiac arrhythmia by administering to a mammal in need thereof, such as a human in need thereof, an effective amount of an agent identified using the assay described above. Preferably, the inventive methods of preventing or treating cardiac arrhythmia by administering to a mammal in need thereof, such as a human in need thereof, an effective amount of an agent which increases the level of surface expression of a first mutant form of hERG, such as G601S or N470D. Even more preferably, such an agent does not increase the level of expression of a second mutant form of hERG, such as G601S/F656C or N470D/F656C.

The preferred embodiments of the present invention also include compositions for preventing or treating cardiac arrhythmia in a mammal, such as a human, comprising an effective amount of such an agent in combination with a pharmaceutically acceptable carrier.

An illustrative example of a particularly preferred agent suitable for use in the therapeutic methods and compositions of the present invention is vanoxerine (also known as GBR-12909). Vanoxerine, its manufacture and/or certain pharmaceutical uses thereof are described in U.S. Pat. Nos. 4,202,896, 4,476,129 and 4,874,765, as well as European Patent EP 243,903 and PCT International Application WO 91/01732.

Pharmaceutically acceptable salts of vanoxerine may also be employed in the methods of the present invention. The pharmaceutically acceptable salts of vanoxerine which may be used in the inventive methods include, but are not limited to, salts of vanoxerine formed from non-toxic inorganic or organic acids. For example, pharmaceutically acceptable salts include, but are not limited to, the following: salts derived from inorganic acids, such as hydrochloric, hydrobromic, sulfuric, sulfamic, phosphoric, nitric and the like; salts derived from organic acids, such as acetic, propionic, succinic, glycolic, stearic, lactic, malic, tartaric, citric, ascorbic, pamoic, maleic, hydroxymaleic, phenylacetic, benzoic, salicylic, sulfanilic, 2-acetoxy-benzoic, fumaric, toluenesulfonic, methanesulfonic, ethane disulfonic, oxalic, isethionic, trifluoroacetic and the like; and salts derived from amino acids, such as glutamic acid or aspartic acid. See U.S. Pat. No. 6,187,802 and WO 91/01732.

The pharmaceutically acceptable salts of vanoxerine useful in the methods of the present invention can be synthesized from vanoxerine by conventional chemical methods. Generally, the salts are prepared either by ion exchange chromatography or by reacting the free base with stoichiometric amounts or with an excess of the desired salt-forming inorganic or organic acid in a suitable solvent or various combinations of solvents.

Pharmaceutically acceptable metabolites of vanoxerine may be employed in the methods of the present invention, provided that they elicit the necessary pharmacological respsonse(s) when administered to a mammal, such as a human, and are otherwise appropriate for use in the invention methods, e.g., exhibit an acceptable toxicology profile, are relatively stable under the conditions of use, etc. Illustrative examples of suitable metabolite which may be employed in the inventive methods include, but are not limited to, the following: 1-[2-(diphenylmethoxy) ethyl]-4-(3-phenylpropyl)piperazine (which is also known as GBR 12935 and is the principal metabolite of vanoxerine in humans) and pharmaceutically acceptable salts, analogs and derivatives thereof.

Pharmaceutically acceptable derivatives of vanoxerine may also be employed in the methods of the present invention, provided that they elicit the necessary pharmacological responses when administered to a mammal, such as a human, and are otherwise appropriate for use in the invention methods, e.g., exhibit an acceptable toxicology profile, are relatively stable under the conditions of use, etc. Illustrative examples of suitable derivatives which may be employed in the inventive methods include, but are not limited to, the following: GBR 13069 and GBR 12783, which are structurally similar to vanoxerine and GBR 12935, respectively, except that the 3-phenylpropyl moiety has been replaced by a 3-phenylpropen-2-yl moiety.

Other suitable derivatives include phenolic derivatives of vanoxerine, i.e. derivatives of vanoxerine in which the unsubstituted phenyl group of vanoxerine is substituted by one or more hydroxy groups, as well as the methoxy congeners thereof. (See Rice et al, "Oxygenated analogues of 1-(2-(diphenylmethoxy)ethyl)- and 1-(2-(bis(4-flourophenyl)methoxy)ethyl)-4-(3-phenylpropyl) piperazines (GBR 12935 and GBR 12909) as Potential Extended-Action Cocaine-Abuse Therapeutic Agents," *J. Med. Chem.* 42(23):5029–5042 (2001); and Dutta et al., "Positional Importance of the Nitrogen Atom in Novel Piperidine Analogs of GBR 12909: Affinity and Selectivity for the Dopamine Transporter," *Med. Chem. Res.* 3(4):209–222 (1993)).

Additional examples of suitable derivatives which may be employed in the methods of the present invention include 4-[2-bis(halophenyl)methoxy]-ethyl]-α-(substituted phenyl)-1-piperazine alkanol derivatives. See, e.g., U.S. Pat. No. 4,476,129.

When employed in the present methods, vanoxerine, or a pharmaceutically acceptable salt, derivative or metabolite thereof, may be administered by any technique capable of introducing a pharmaceutically active agent to the desired site of action, including, but not limited to, buccal, sublingual, nasal, oral, topical, rectal and parenteral administration. Delivery of the compound may also be through the use of controlled release formulations in subcutaneous implants or transdermal patches.

For oral administration, a suitable composition containing vanoxerine, or a pharmaceutically acceptable salt, derivative or metabolite thereof, may be prepared in the form of tablets, dragees, capsules, syrups and aqueous or oil suspensions. The inert ingredients used in the preparation of these compositions are known in the art. For example, tablets may be prepared by mixing the active compound with an inert diluent, such as lactose or calcium phosphate, in the presence of a disintegrating agent, such as potato starch or microcrystalline cellulose, and a lubricating agent, such as magnesium stearate or talc, and then tableting the mixture by known methods.

Tablets may also be formulated in a manner known in the art so as to give a sustained release of vanoxerine, or a pharmaceutically acceptable salt, derivative or metabolite thereof. Such tablets may, if desired, be provided with enteric coatings by known method, for example by the use of cellulose acetate phthalate. Suitable binding or granulating agents include, but are not limited to gelatine, sodium carboxymethylcellulose, methylcellulose, polyvinylpyrrolidone or starch gum. Talc, colloidal silicic acid, stearin as well as calcium and magnesium stearate or the like can be used as anti-adhesive and gliding agents.

Tablets may also be prepared by wet granulation and subsequent compression. A mixture containing the vanoxerine, or a pharmaceutically acceptable salt, derivative or metabolite thereof, and at least one diluent, and optionally a part of the disintegrating agent, is granulated together with an aqueous, ethanolic or aqueous-ethanolic solution of the binding agents in an appropriate equipment, then the granulate is dried. Thereafter, other preservative, surface acting, dispersing, disintegrating, gliding and anti-adhesive additives can be mixed to the dried granulate and the mixture can be compressed to tablets or capsules.

The tablets may also be prepared by the direct compression of the mixture containing the active ingredient together with the needed additives. If desired, the tablets may be transformed to dragees by using protective, flavoring and dyeing agents such as sugar, cellulose derivatives (methyl- or ethylcellulose or sodium carboxymethylcellulose), polyvinylpyrrolidone, calcium phosphate, calcium carbonate, food dyes, aromatizing agents, iron oxide pigments and the like which are commonly used in the pharmaceutical industry.

For the preparation of capsules or caplets, a mixture of vanoxerine, or a pharmaceutically acceptable salt, derivative or metabolite thereof, and the desired additives may be filled into a capsule, such as a hard or soft gelatin capsule. The contents of a capsule and/or caplet may also be formulated using known methods to give sustained release of the active compound.

Liquid oral dosage forms of vanoxerine, or a pharmaceutically acceptable salt, derivative or metabolite thereof, may be an elixir, suspension and/or syrup, where the compound is mixed with a non-toxic suspending agent. Liquid oral dosage forms may also comprise one or mote sweetening agent, flavoring agent, preservative and/or mixture thereof.

For rectal administration, a suitable composition containing vanoxerine, or a pharmaceutically acceptable salt, derivative or metabolite thereof, may be prepared in the form of a suppository. In addition to the active ingredient, the suppository may contain a suppository mass commonly used in pharmaceutical practice, such as Theobroma oil, glycerinated gelatin or a high molecular weight polyethylene glycol.

For parenteral administration, a suitable composition of vanoxerine, or a pharmaceutically acceptable salt, derivative or metabolite thereof, may be prepared in the form of an injectable solution or suspension. For the preparation of injectable solutions or suspensions, the active ingredients can be dissolved in aqueous or non-aqueous isotonic sterile injection solutions or suspensions, such as glycol ethers, or optionally in the presence of solubilizing agents such as polyoxyethylene sorbitan monolaurate, monooleate or monostearate. These solutions or suspension may be prepared from sterile powders or granules having one or more carriers or diluents mentioned for use in the formulations for oral administration. Parenteral administration may be through intravenous, intradermal, intramuscular or subcutaneous injections.

A composition containing vanoxerine, or a pharmaceutically acceptable salt, derivative or metabolite thereof, may also be administered nasally, for example by sprays, aerosols, nebulised solutions and/or powders. Metered dose systems known to those in the art may also be used.

Pharmaceutical compositions of vanoxerine, or a pharmaceutically acceptable salt, derivative or metabolite thereof, may be administered to the buccal cavity (for example, sublingually) in known pharmaceutical forms for such administration, such as slow dissolving tablets, chewing gums, troches, lozenges, pastilles, gels, pastes, mouthwashes, rinses and/or powders.

Compositions containing vanoxerine, or a pharmaceutically acceptable salt, derivative or metabolite thereof, for topical administration may comprise a matrix in which the pharmacologically active compound is dispersed such that it is held in contact with the skin in order to administer the compound transdermally. A suitable transdermal composition may be prepared by mixing vanoxerine, or a pharmaceutically acceptable salt, derivative or metabolite thereof, with a topical vehicle, such as a mineral oil, petrolatum and/or a wax, for example paraffin wax or beeswax, together with a potential transdermal accelerant such as dimethyl sulphoxide or propylene glycol. Alternatively, vanoxerine, or a pharmaceutically acceptable salt, derivative or metabolite thereof, may be dispersed in a pharmaceutically acceptable cream or ointment base. The amount of vanoxerine, or a pharmaceutically acceptable salt, derivative or metabolite thereof, contained in a topical formulation should be such that a therapeutically effective amount delivered during the period of time for which the topical formulation is intended to be on the skin.

Vanoxerine, or a pharmaceutically acceptable salt, derivative or metabolite thereof, may also be administered by continuous infusion either from an external source, for example by intravenous infusion or from a source of the compound placed within the body. Internal sources include implanted reservoirs containing the vanoxerine, or a pharmaceutically acceptable salt, derivative or metabolite thereof, to be infused which is continuously released for example by osmosis and implants which may be (a) liquid such as a suspension or solution in a pharmaceutically acceptable oil of the compound to be infused for example in the form of a very sparingly water-soluble derivative such as a dodecanoate salt or (b) solid in the form of an implanted support, for example of a synthetic resin or waxy material, for the compound to be infused. The support may be a single body containing all the compound or a series of several bodies each containing part of the compound to be delivered. The amount of vanoxerine, or a pharmaceutically acceptable salt, derivative or metabolite thereof, present in an internal source should be such that a therapeutically effective amount is delivered over a long period of time.

In addition, an injectable solution of vanoxerine, or a pharmaceutically acceptable salt, derivative or metabolite thereof, can contain various additives such as preservatives, such as benzyl alcohol, methyl or propyl 4-hydroxybenzoate, benzalkonium chloride, phenylmercury borate and the like; as well as antioxidants, such as ascorbic acid, tocopherol, sodium pyrosulfate and optionally complex forming agents, such as an ethylenediamine tetraacetate salt for binding the metal traces, as well as buffers for adjusting the pH value and optionally a local anaesthetizing agent, e.g. lidocaine. The injectable solution containing vanoxerine, or a pharmaceutically acceptable salt, derivative or metabolite thereof, is filtered before filling into the ampule and sterilized after filling.

Other agents which could be used in such therapeutic methods of the present invention include any of the known blockers of hERG, such as astermizole, terfenadine, E-4031, cisapride, chloroquine and the like.

EXAMPLES

Example 1

Rescue of hERG-G601S Surface Expression by Astemizole

HEK-293 cells stably expressing hERG-G601S-HA were plated in a BIOCOAT poly-D-lysine cellware 96-well black plate with a clear bottom (BD Discovery Labware). Cells were plated ($8 \times 10^4$ cells/well) in complete medium containing DMEM/F12 with 10% FBS plus penicillin-streptomycin and geneticin (G418; 0.5 mg/ml) and incubated for 8 hours at 37° C./5% $CO_2$ prior to addition of drugs. Stock solutions (200 μM, 1 mM and 5 mM) of the drugs (astemizole, norastemizole, fexofenadine) were prepared. Just prior to addition, working dilutions (200 nM, 1μM and 5μM) were prepared in DMEM/F12 with 10% FBS. Vehicle consisted of 0.1% DMSO in DMEM/F12 with 10% FBS. The media bathing the cells was removed and replaced with drug containing or vehicle control media (100 μl/well). For each drug there were three test wells for each concentration and three control wells. The plates were incubated overnight (approx. 16 hours) at 37° C./5% $CO_2$ prior to the start of the surface expression assay.

Surface expression assays were performed on the bench top at room temperature. The cells were washed three times with 100 μl PBS, followed by fizeation with freshly prepared, ice-cold 4% paraformaldehyde in PBS (pH 7.2, 100 μl, 20 min.) The fixative was removed and the cells rinsed with 100 μl PBS. Nonspecific binding sites on the cells were blocked by incubation with 1% goat serum in pBS (blocking buffer, 100 μl for 30 min). Blocking buffer was removed and the cells incubated for three hours with rat anti-HA (1:500 dilution, 100 μl, Roche) diluted in blocking buffer. After removing the primary antibody, the cells were washed three times with 1% goat serum in PBS (100 μl and 10 min/wash). HRP-conjugated goat anti-rat antibody (1:2000; Jackson Labs) was diluted win blocking buffer and incubated with the cells for 1 hour (100 μl/well). Following incubation, cells were washed with 100 μl of 1% goat serum in PBS (10 min) and then three times with 100 μl PBS (10 min/wash).

Chemiluminescent signals were developed with the SuperSignal ELISA Femto Maximum Sensitivity Substrate (Pierce Chemical Co.). PBS was removed from the wells and replaced with 100 μl detection reagent per well. Signals were immediately captured using a GloRunner luminometer (Turner Designs).

The data obtained showed a direct correlation between the ability of a drug to rescue surface expression of hERG-G601S-HA and the potency with which it blocks hERG. Thus, astemizole increased surface expression much more than norastemizole, which is a much weaker blocker. Similarly, fexofenadine, which does not block hERG at all, did not increase surface expression of hERG-G601S-HA.

Example 2

Removal of the Drug Binding Site in hERG Removes Rescue by Astemizole

HEK-293 cells in 35 mm dishes were transiently transfected with cDNAs encoding hERG-G601S-HA or hERG-G601S/F656C-HA. Twenty-four hours post-transfection, astemizole (1 μM) was added to some plates and vehicle control (DMSO) added to others and the plates incubated overnight.

Following incubation, the cells were fixed with paraformaldehyde and processed for surface expression of the HA tag as described above (with the exception of proportionally larger reagent volumes). Chemiluminescent signals were developed in a TD20/20 luminometer (Turner Biosystems).

The data obtained showed that astemizole did not rescue expression of the double mutant hERG-G601S/F656C, but did rescue expression of hERG-G601S, showing that it is a potent blocker of hERG.

Having now fully described this invention, it will be understood to those of ordinary skill in the art that the methods of the present invention can be carried out with a wide and equivalent range of conditions, formulations, and other parameters without departing from the scope of the invention or any embodiments thereof.

All patents and publications cited herein are hereby fully incorporated by reference in their entirety. The citation of any publication is for its disclosure prior to the filing date and should not be construed as an admission that such publication is prior art or that the present invention is not entitled to antedate such publication by virtue of prior invention.

What is claimed is:

1. A method of identifying an agent that alters the level of surface expression of an integral membrane protein in a mammalian cell, said method comprising:
    a) preparing a first medium containing mammalian cells that express a first mutant form of said membrane protein, wherein said first mutant form is expressed on the surface of said cells at a level less than a wild-type form of said protein;
    b) adding to said first medium containing mammalian cells a test amount of a candidate agent;
    c) incubating said cells in the presence of said candidate agent for a predetermined period of time;
    d) adding to said first medium containing mammalian cells at least one antibody which binds to at least one extracellular epitope of said mutant form of said membrane protein; and
    e) determining the level of binding of said at least one antibody to said extracellular epitope, wherein a change in said level of binding relative to a first control indicates that said candidate agent alters the level of surface expression of said mutant form of said membrane protein, wherein said first control comprises said first medium containing mammalian cells that express said first mutant form of said membrane protein in an amount equal to that in step (a) and said at least one antibody in an amount equal to that added in step (d).

2. The method according to claim 1, further comprising the steps of:
    (f) preparing a second medium containing mammalian cells that express a second mutant form of said membrane protein, said second mutant form is different from said first mutant form and is expressed on the surface of said mammalian cells at a level lower than that of a wild-type form of said membrane protein;
    (g) adding to said second medium containing mammalian cells an amount of said candidate agent equal to that used in step (b);
    (h) incubating said cells in the presence of said candidate agent for a predetermined period of time;
    (i) adding to said second medium containing mammalian cells at least one antibody which binds to at least one extracellular epitope of said second mutant form of said membrane protein; and
    (j) determining the level of binding of said at least one antibody to said extracellular epitope of said second mutant form of said membrane protein,
    wherein a change in said level of binding relative to a second control indicates that said candidate agent alters the level of surface expression of said second mutant form of said membrane protein, wherein said second control contains said second medium containing mammalian cells that express said second mutant form of said membrane protein in an amount equal to that in step (f) and said at least one antibody in an amount equal to that added in step (i).

3. The method according to claim 1, further comprising the steps of:
    (f) preparing a second medium containing mammalian cells that express a wild-type form of said membrane protein;
    (g) adding to said second medium containing mammalian cells an amount of said candidate agent equal to that used in step (b);

(h) incubating said cells in the presence of said candidate agent for a predetermined period of time;

(i) adding to said second medium containing mammalian cells at least one antibody which binds to at least one extracellular epitope of said wild-type form of said membrane protein; and (j) determining the level of binding of said at least one antibody to said extracellular epitope of said wild-type form of said membrane protein, wherein a change in said level of binding relative to a second control indicates that said candidate agent alters the level of surface expression of said wild-type form of said membrane protein, wherein said second control contains said second medium containing mammalian cells that express said wild type form of said membrane protein in an amount equal to that in step (f) and said at least one antibody in an amount equal to that added in step (i).

4. The method according to claim 1 or 3, wherein step (d) comprises adding an effective amount of at least one primary antibody and an effective amount of at least one secondary antibody, wherein said primary antibody binds to at least one extracellular epitope of said first mutant form of said membrane protein and said secondary antibody binds to said primary antibody.

5. The method according to claim 1 or 3, wherein said level of binding is measured by fluorescence, luminescence, radioactivity, absorbance or a combination of two or more thereof.

6. The method according to claim 1 or 3, wherein said integral membrane protein is a membrane ion channel.

7. The method according to claim 4, wherein said membrane ion channel is a sodium channel, a potassium channel, a calcium channel or a chloride channel.

8. The method according to claim 1, wherein said at least one extracellular epitope comprises a wild-type epitope.

9. The method according to claim 1, wherein said at least one extracellular epitope contains a tag.

10. The method according to claim 9, wherein said extracellular tag replaces at least a portion of an extracellular domain of said integral membrane protein.

11. The method according to claim 9, wherein said extracellular tag is inserted in an extracellular domain of said membrane protein.

12. The method according to claim 9, wherein said extracellular tag comprises a hemagglutinin (HA) tag.

13. The method according to claim 4, wherein said secondary antibody is coupled to an enzyme to facilitate determining the level of binding of the secondary antibody to the primary antibody.

14. The method according to claim 13, wherein said enzyme is selected from the group consisting of peroxidases, luciferases, alkaline phosphatases, glucose oxidases, beta-galactosidases and mixtures of two or more thereof.

15. The method according to claim 1 or 3, wherein said first mutant form comprises an amino acid sequence which differs in at least one amino acid residue from the amino acid sequence of a wild-type form of said membrane protein.

16. The method according to claim 2, wherein said second mutant form comprises an amino acid sequence which differs in at least one amino acid residue from the amino acid sequence of a wild-type form of said membrane protein.

17. The method according to claim 1 or 3, wherein said first mutant form is a trafficking-deficient mutant.

18. The method according to claim 2, wherein said second mutant form is a trafficking-deficient mutant.

19. The method according to claim 1 or 3, wherein said membrane protein is a potassium ion channel.

20. The method according to claim 19, wherein said potassium ion channel is hERG.

21. The method according to claim 20, wherein said first mutant form of hERG is G601S.

22. The method according to claim 20, wherein said first mutant form of hERG is N470D.

23. The method according to claim 2, wherein said second mutant form of said membrane protein is hERG G601S/F656C.

24. The method according to claim 2, wherein said second mutant form of said membrane protein is hERG N470D/F656C.

* * * * *